US00PP29320P3

(12) United States Plant Patent
Suzuki

(10) Patent No.: US PP29,320 P3
(45) Date of Patent: May 29, 2018

(54) ***LOROPETALUM* PLANT NAMED 'GEKKOU'**

(50) Latin Name: *Loropetalum chinense*
Varietal Denomination: Gekkou

(71) Applicant: Yuji Suzuki, Kawaguchi (JP)

(72) Inventor: Yuji Suzuki, Kawaguchi (JP)

( * ) Notice: Subject to any disclaimer, the term of this patent is extended or adjusted under 35 U.S.C. 154(b) by 44 days.

(21) Appl. No.: 14/999,704

(22) Filed: Jun. 15, 2016

(65) Prior Publication Data

US 2017/0367233 P1 Dec. 21, 2017

(51) Int. Cl.
*A01H 5/02* (2018.01)
*A01H 5/12* (2018.01)

(52) U.S. Cl.
USPC ..... Plt./226
CPC ..... *A01H 5/02* (2013.01); *A01H 5/12* (2013.01)

(58) Field of Classification Search
None
See application file for complete search history.

*Primary Examiner* — Anne Marie Grunberg
(74) *Attorney, Agent, or Firm* — Cassandra Bright

(57) ABSTRACT

A new and distinct *Loropetalum* cultivar named 'Gekkou' is disclosed, characterized by bright deep pink flowers and strong heat tolerance and resistance to color change in extreme temperatures. Plant habit is very dense and full growing with very vibrant burgundy foliage. The new variety is a *Loropetalum*, normally produced as an outdoor garden or container plant.

3 Drawing Sheets

Latin name of the genus and species: *Loropetalum chinense.*

Variety denomination: 'Gekkou'.

BACKGROUND OF THE INVENTION

The new *Loropetalum* cultivar is a product of a planned breeding program conducted by the inventor in Kawaguchi City, Saitama, Japan. The objective of the breeding program was to produce new *Loropetalum* varieties with better foliage color and improved flowering for ornamental commercial applications. The cross resulting in this new variety was made during Jun. 30, 2013.

The seed parent is the commercial variety referred to as *Loropetalum* 'Beniotome', unpatented. The pollen parent is the unpatented, propriety variety referred to as *Loropetalum* '5-47'. The new variety was selected by the inventor in a group of seedlings resulting from the 2005 crossing, in a nursery in Kawaguchi City, Saitama, Japan.

Asexual reproduction of the new cultivar was performed by softwood terminal cuttings. This was first performed at a nursery in Kawaguchi City, Saitama, Japan, in June 2013 and has shown that the unique features of this cultivar are stable and reproduced true to type in 5 successive generations.

SUMMARY OF THE INVENTION

The cultivar 'Gekkou' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Gekkou' These characteristics in combination distinguish 'Gekkou' as a new and distinct *Loropetalum* cultivar:

1. Bright deep pink flowers.
2. Strong heat tolerance and resistant to color change in extreme temperatures.
3. Very dense and full growing plant.
4. Vibrant burgundy foliage.

Plants of the new cultivar 'Gekkou' are similar to plants of the seed parent, *Loropetalum* 'Beniotome' in most horticultural characteristics, however, plants of the new cultivar 'Gekkou' differ in the following;

1. The new variety has dark bright deep pink flowers, parent variety has red to magenta colored flowers.
2. The new variety has significantly more flowers than the parent variety.

Plants of the new cultivar 'Gekkou' are similar to plants of the pollen parent, *Loropetalum* '5-47' in most horticultural characteristics, however, plants of the new cultivar 'Gekkou' differ in the following;

1. The new variety has large flowers, whereas the parent has medium sized flowers.
2. Bright magenta deep pink flowers, the parent has lighter pink flowers.

COMMERCIAL COMPARISON

Plants of the new cultivar 'Gekkou' are comparable to the patented, commercial variety *Loropetalum* 'Kurenai Daiou', U.S. Plant Pat. No. 27,748. The two *Loropetalum* varieties are similar in most horticultural characteristics; however, the new variety 'Gekkou' differs in the following:

1. The new variety has smaller foliage.
2. The new variety has smaller flowers than this comparator.

BRIEF DESCRIPTION OF THE PHOTOGRAPHS

The accompanying photograph in FIG. 1 illustrates in full color an overhead view of a typical plant of 'Gekkou' grown in a 1 gallon pot.

Figure 1:
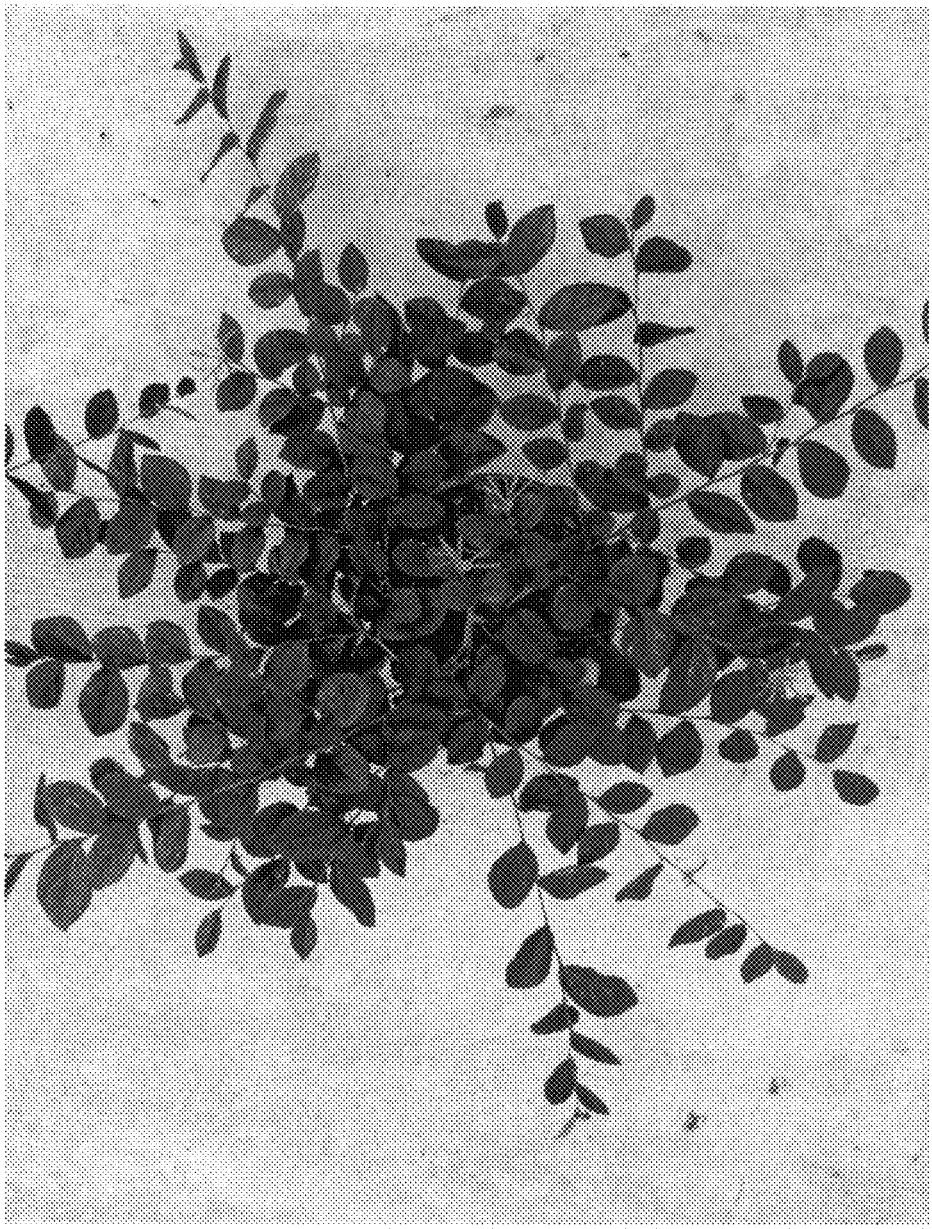
Figure 2:
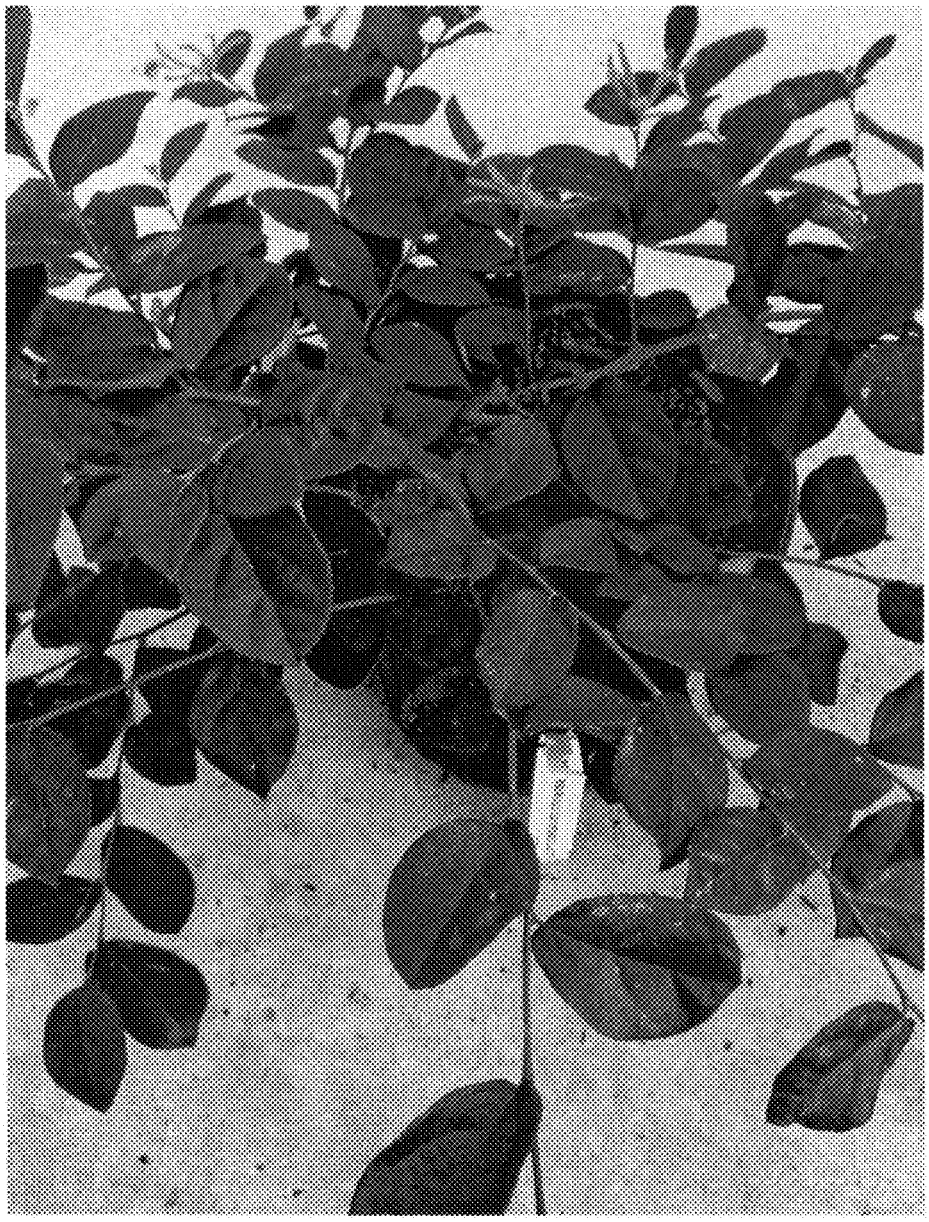
FIG. 2 illustrates a side of of the same plant.
Figure 3:
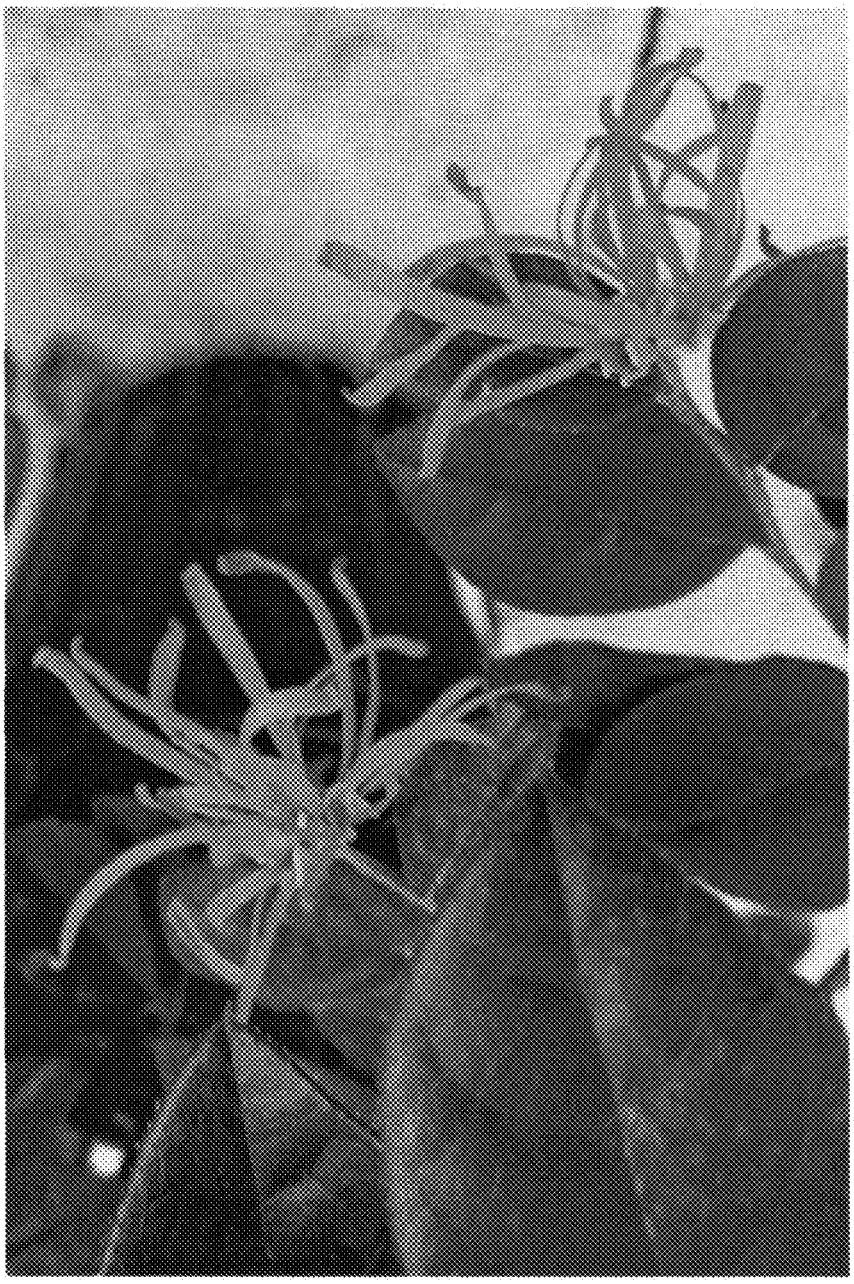
FIG. 3 illustrates a close up view of the flowers and foliage. Age of the plant photographed is approximately 1 to 2 years old from a rooted cutting.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Gekkou' plants grown in a double poly greenhouse, in Grand Haven, Mich. The growing temperature averaged from 60-65° F. during the day and from 40-50° F. during the night. The double poly was present from Fall through Winter, then removed in the Spring. Shade cloth was used through the Summer. Measurements and numerical values represent averages of typical plant types.

Botanical classification: *Loropetalum chinense* 'Gekkou'.

PROPAGATION

Type of propagation typically used: Cutting.
Time to initiate roots: 18 days at 27° C.
Number of days to produce a rooted liner in summer: 110 days at 27° C.
Root description: Thin to thick, fibrous, free branching and fleshy. New roots are purple in color, aging to brown.

PLANT

Type of plant: Perennial shrub.
Age of plant described: 1 to 2 years old.
Container size of the plant described: 1 gallon pot.
Growth habit: Spreading to upright.
Height: 17 cm.
Plant spread: 29 cm.
Growth rate: Moderate.
Plant vigor: Good.
Branching characteristics: Lateral branching.
Characteristics of primary lateral branches:
- *Length*.—Average 18 cm.
- *Quantity*.—11.
- *Diameter*.—3.0 mm.
- *Color*.—Young stems: Near RHS Brown 200B. Older stems: Near RHS Greyed-Orange 165A.
- *Aspect*.—Straight, occurring at various angles from acute to obtuse.
- *Strength*.—Good.

Internode length: 2.1 cm.
Stem pubescence: Yes.

FOLIAGE

Leaf:
- *Arrangement*.—Alternate, single.
- *Quantity*.—Approximately 43 per branch.
- *Average length*.—2.2-5.8 cm.
- *Average width*.—1.6-3.4 cm.
- *Shape of blade*.—Ovate rounded.
- *Apex*.—Acute.
- *Base*.—Oblique.
- *Margin*.—Entire.
- *Texture of top surface*.—Rough due to presence of pubescence.
- *Texture of bottom surface*.—Ribbed due to protruding veins. Moderate pubescence.
- *Appearance*.—Upper surface: heavy pubescence on young leaves, moderate to slight on older leaves. Lower surface: moderate to strong pubescence at all ages.
- *Color*.—Young foliage upper side: Near RHS Greyed-purple 187A. Young foliage under side: Glaucous. Near RHS Red-purple 59A. Mature foliage upper side: Near RHS Greyed-Purple 187A with undertones of RHS Black 200A. Mature foliage under side: Glaucous. Near RHS Red-Purple 59B with undertones of RHS Greyed-Green 191D.
- *Venation*.—Type: Pinnate. Venation color upper side: Midribs and veins are depressed on the upper side. Color does not differ from the leaf color. Venation color under side: Midribs and veins are prominent on the underside. Near RHS Greyed-Purple Group 186A.
- *Petiole*.—Length: 0.2 to 0.3 cm. Diameter: 1 mm. Color: Near RHS Greyed-Orange 166A.

FLOWER

Inflorescence and flower type and habit: Mainly terminal with umbel inflorescence.
Quantity of flowers per inflorescence: 5 to 7.
Flower type: Strap-shaped.
Flower aspect: Upright.
Quantity of flowers per lateral stem: 15-30.
Quantity of flowers per plant: 50-200 on a plant of 1 to 2 years.
Natural flowering season: Spring to Fall.
Fragrance: None.
Bud:
- *Shape*.—Obovate.
- *Length*.—4 mm.
- *Diameter*.—2.5 mm.
- *Color*.—Near RHS Red-Purple 59B.

Petals:
- *Quantity per flower*.—4.
- *Shape*.—Linear.
- *Margin*.—Entire.
- *Texture*.—Smooth, silky.
- *Appearance*.—Ribbon-like.
- *Length*.—17 mm.
- *Width*.—1 mm.
- *Tip*.—Truncate.
- *Color*.—When opening: Upper surface: Near RHS Red-Purple 60B. Lower surface: Near RHS Red-Purple 60B. Fully opened: Upper surface: Near RHS Red-Purple 60B. Lower surface: Near RHS Red-Purple 60B. Fades to: Near RHS Red-Purple 60B.

Sepals:
- *Quantity per flower*.—4-6.
- *Appearance*.—Slightly pubescent.
- *Texture*.—Slightly pubescent.
- *Arrangement*.—Whorl.
- *Shape*.—Ovate and fused, slightly curled outward.
- *Length*.—4 mm.
- *Width*.—2 mm.
- *Tip*.—Slightly reflexed.

*Base*.—Fused.

*Margin*.—Entire, smooth.

*Color*.—Immature upper and lower side: Near RHS Red-Purple 58A. Mature upper and lower side: Near RHS Red-Purple 58A.

REPRODUCTIVE ORGANS

Stamens:

*Number*.—4.

*Filament length*.—Average 1 mm.

*Filament color*.—Near RHS White 155C.

*Anthers*.—Shape: Linear. Length: Less than 1 mm. Color: Near RHS White 155C.

*Pollen*.—Amount: Scant. Color: Near RHS White 155B.

Pistil:

*Number*.—2.

*Length*.—Approximately 1 mm.

*Style*.—Length: Less than 1 mm. Color: Near RHS White 155C.

*Stigma*.—Shape: Linear. Color: Near RHS White 155C. Ovary: Less than 1 mm, colored near Yellow-Green 150D.

OTHER CHARACTERISTICS

Lowest temperature tolerance: 5 to 10° F.

Disease/pest resistance: No unusual susceptibility to diseases or pests noted to date.

What is claimed is:

1. A new and distinct cultivar of *Loropetalum* plant named 'Gekkou' as herein illustrated and described.

* * * * *